United States Patent
Myers et al.

(10) Patent No.: US 8,895,797 B2
(45) Date of Patent: Nov. 25, 2014

(54) PROCESS FOR DEHYDROGENATION OF HYDROCARBONS IN A MULTI-STAGE FLUIDIZED BED REACTOR

(75) Inventors: David N. Myers, Hoffman Estates, IL (US); Lev Davydov, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 619 days.

(21) Appl. No.: 12/749,544

(22) Filed: Mar. 30, 2010

(65) Prior Publication Data

US 2011/0245557 A1 Oct. 6, 2011

(51) Int. Cl.
*C07C 5/333* (2006.01)

(52) U.S. Cl.
USPC ........... 585/659; 585/301; 585/302; 585/654; 585/926

(58) Field of Classification Search
USPC .................................. 585/654, 659, 601, 302
See application file for complete search history.

(56) References Cited

U.S. PATENT DOCUMENTS

| | | | | |
|---|---|---|---|---|
| 2,397,352 A | * | 3/1946 | Hemminger | 585/659 |
| 2,664,967 A | * | 1/1954 | Molstedt | 95/184 |
| 3,669,877 A | * | 6/1972 | Friedrich | 208/164 |
| 3,706,536 A | * | 12/1972 | Greenwood et al. | 422/634 |
| 4,133,743 A | * | 1/1979 | Boret et al. | 208/64 |
| 4,277,444 A | * | 7/1981 | Van Landeghem | 422/634 |
| 4,513,162 A | * | 4/1985 | Al-Muddarris | 585/654 |
| 4,996,387 A | * | 2/1991 | Gerhold et al. | 585/654 |
| 5,336,829 A | * | 8/1994 | Boitiaux et al. | 585/659 |
| 5,491,275 A | | 2/1996 | Vora et al. | |
| 5,689,029 A | | 11/1997 | Vora et al. | |
| 5,811,622 A | | 9/1998 | Oroskar | |
| 6,191,332 B1 | * | 2/2001 | Duee et al. | 585/654 |

FOREIGN PATENT DOCUMENTS

GB 762017 * 11/1956

OTHER PUBLICATIONS

U.S. Appl. No. 12/749,542, filed Mar. 30, 2010, Myers et al.

* cited by examiner

*Primary Examiner* — In Suk Bullock
*Assistant Examiner* — Bradley Etherton
(74) *Attorney, Agent, or Firm* — Arthur E Gooding

(57) ABSTRACT

A reactor design and process for the dehydrogenation of hydrocarbons is presented. The reactor design includes a multibed catalytic reactor, where each of the reactor beds are fluidized. The catalyst in the reactor cascades through the reactor beds, with fresh catalyst input into the first reactor bed, and the spent catalyst withdrawn from the last reactor bed. The hydrocarbon feedstream is input to the reactor beds in a parallel formation, thereby decreasing the thermal residence time of the hydrocarbons when compared with a single bed fluidized reactor, or a series reactor scheme.

19 Claims, 3 Drawing Sheets

PROCESS FOR DEHYDROGENATION OF HYDROCARBONS IN A MULTI-STAGE FLUIDIZED BED REACTOR

FIELD OF THE INVENTION

The present invention relates to the production of light olefins from paraffins. Specifically, the invention is directed at propane dehydrogenation in the production of propylene.

BACKGROUND OF THE INVENTION

Continuous catalyst conversion processes are common in the refining and petrochemical industry. The fluidized catalyst cracking of hydrocarbons is an important process for the production of lighter hydrocarbon components, and as such, it is an important process for the production of propylene. The fluidized catalytic cracking process continuously circulates a fluidized catalyst between a reactor and a regenerator.

Another route for the production of propylene can be obtained by the dehydrogenation of propane through catalytic dehydrogenation. The dehydrogenation catalysts generally comprise noble metal catalysts on acidic supports, such as alumina, or silica alumina, or zeolitic materials. However, the reaction is strongly endothermic, and requires a high temperature for the reaction to proceed at a satisfactory rate. At the same time, the reactions need to be controlled to limit the degradation of the propane to form methane and ethylene, and where the ethylene can be hydrogenated by the hydrogen released through the dehydrogenation of the propane. The process also leads to coking of the catalyst, and deactivates the catalyst. The catalyst therefore needs to be regenerated on a regular basis after relatively short periods of operation, or residence, in the dehydrogenation reactor.

The production of propylene through dehydrogenation is an endothermic process and requires a substantial amount of additional heating to allow the process to proceed. As a result, overall selectivity typically suffers due to temperature gradients across the catalyst bed. The hottest temperatures are desired at the outlet of the catalyst bed, but is not achievable with current state-of-the-art designs. Another problem is the excessive non-catalytic thermal residence time, due to the required heating of the feed prior to feeding into the reactor.

SUMMARY OF THE INVENTION

The present invention provides for a new process for the dehydrogenation of a hydrocarbon feedstream. The hydrocarbon feedstream comprising paraffins is passed in parallel streams to a plurality of catalytic reactor beds. The reactor comprising a plurality of fluidized reactor beds, where the catalyst flows through the reactor cascading from one reactor bed to a subsequent reactor bed. The catalyst flows through the reactor beds in series, where the catalyst undergoes some deactivation with each reactor bed that the catalyst passes through. Regenerated catalyst is passed to the first reactor bed, and the catalyst from the first reactor bed is passed to a second reactor bed, with the catalyst from the second reactor bed continuing on to the next reactor bed in the series. The catalyst leaving the last reactor bed is passed to a regeneration unit, thereby creating regenerated catalyst to be passed to the first reactor bed. The process reduces the thermal residence time and the reduction in the thermal residence time provides for another benefit, in that a fired heater is no longer needed. The necessary heat for the reaction is provided for by the heated catalyst returning from the regeneration unit. There is also a lower capital and real estate requirement. Eliminating high temperature thermal residence time minimizes thermal cracking of the feed, and improves the overall product selectivity.

In one embodiment, the process includes passing catalyst from an outlet of a reactor bed back to the inlet of the reactor bed, thereby provided a recycling of catalyst to an individual bed. The recycled catalyst can also be passed through a heating unit, or cooling unit before reentering the catalyst into the reactor bed.

Additional objects, embodiments and details of this invention can be obtained from the following drawings and detailed description of the invention.

DETAILED DESCRIPTION OF THE INVENTION

The present invention is a new design for a dehydrogenation reactor. The new design allows for lower hydrogen partial pressure requirements, and reduces thermal residence times by allowing the reactor beds to operate with a staggered temperature profile with a lower average bed temperature than what could be achieved in a single fluidized bed reactor or by passing the feed and resultant products over a plurality of beds in series. By a plurality of beds, it is meant to indicate two or more beds. The design comprises multiple reactor beds that cascade the flow of the catalyst through the reactor, while having the hydrocarbon feedstream split, and directed to pass through the reactor beds in parallel. This reduces thermal residence times of the hydrocarbon feedstream, and the resulting product stream. A specific embodiment of the present invention is the production of propylene from a propane feedstock. Propane dehydrogenation is an important source of propylene for use as the building block for polypropylene.

Figure 1:
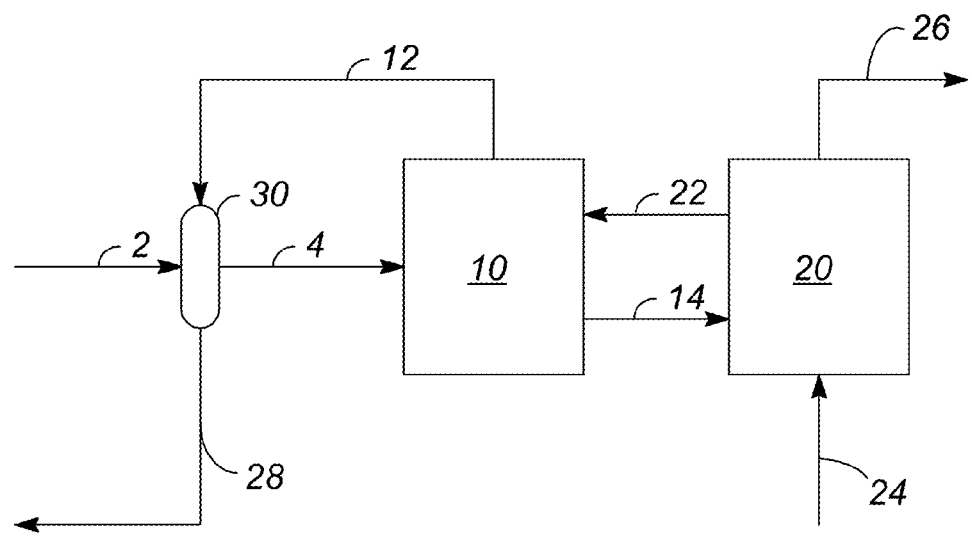
FIG. 1 is a schematic of a plant design for a hydrocarbon dehydrogenation process.

The present invention comprises a multi-stage fluidized bed reactor. The multi-stage reactor comprises a plurality of reactor beds in a parallel configuration, comprising a first reactor bed and at least one subsequent reactor bed. Each reactor bed has a catalyst inlet and a catalyst outlet, and a hydrocarbon feedstream inlet. The reactor further includes a catalyst disengagement section for separating catalyst from a vapor product stream. The dehydrogenation process as shown in FIG. 1 comprises passing a hydrocarbon feedstream 2 to a preheater 30. The preheated feedstream 4 is passed to the dehydrogenation reactor 10, where a product stream 12 comprising olefins is generated. The product stream 12 is passed through the preheater 30 to form a cooled product stream 28 and the preheated feedstream 4. A spent catalyst stream 14 is passed to a regeneration unit 20, where the catalyst is regenerated and the regenerated catalyst stream 22 is passed back to the dehydrogenation reactor 10. Regeneration of the catalyst typically comprises burning off carbon deposits on the catalyst and heating the catalyst for use in the dehydrogenation reactor 10. The regeneration unit 20 includes a regeneration gas inlet 24, and a combustion gas outlet 26. The regeneration unit 20 is known in the art, where an oxygen containing gas is used to combust carbon deposits on the catalyst to return the catalyst to a regenerated state.

In one embodiment, the reactor further includes a catalyst recirculation channel for each reactor bed, wherein each recirculation channel has a channel inlet in fluid communication with the reactor bed catalyst outlet and a channel outlet in fluid communication with each reactor bed catalyst inlet. Optionally, each recirculation channel can further include a heating unit for heating catalyst in each recirculation channel. The dehydrogenation reaction is an endothermic reaction, and the recirculation channel provides heat control to the reactor by adding supplemental heat to the catalyst as the catalyst is recirculated.

This design allows for a staggered temperature profile across the entire reactor, and allows for an increasing temperature profile for each subsequent reactor bed, thereby increasing the yield per reactor bed as the catalyst becomes less active as it passes from one reactor bed to a subsequent reactor bed. This increases selectivities and conversions of the hydrocarbon feedstream. This design also minimizes the hot residence time of the feedstream since only approximately ⅓ of the feedstream is in contact with the hottest catalyst bed temperature.

In one embodiment, the design is aimed at the control of the reactor bed temperatures. The regenerated catalyst is divided and a portion is routed to each of the individual reactor beds. For a case that results in an ascending temperature profile, the catalyst is divided into approximately three equal portions, with one portion passed to each reactor bed. The catalyst recirculation channels, or recirculation pipes, are adjusted to have circulation rates consistent with an operation of the reactor such that each reactor bed has approximately the same density.

As an alternate operation, the temperature of the reactor beds can be controlled through heating of the catalyst in the recirculation channels. Differential heat can be provided to heating the recirculation channels, to provide an ascending temperature profile across the reactor beds. The recirculation rates of the catalyst through the recirculation channels can be adjusted to maintain the desired catalyst bed densities. Vigorous catalyst mixing, associated with fluidized beds, assures that the hot regenerated catalyst quickly imparts its sensible heat into the respective reactor bed. In turn, the absence of intrabed temperature gradients leads to enhanced conversion, selectivity and prolonged catalyst life.

Figure 2:
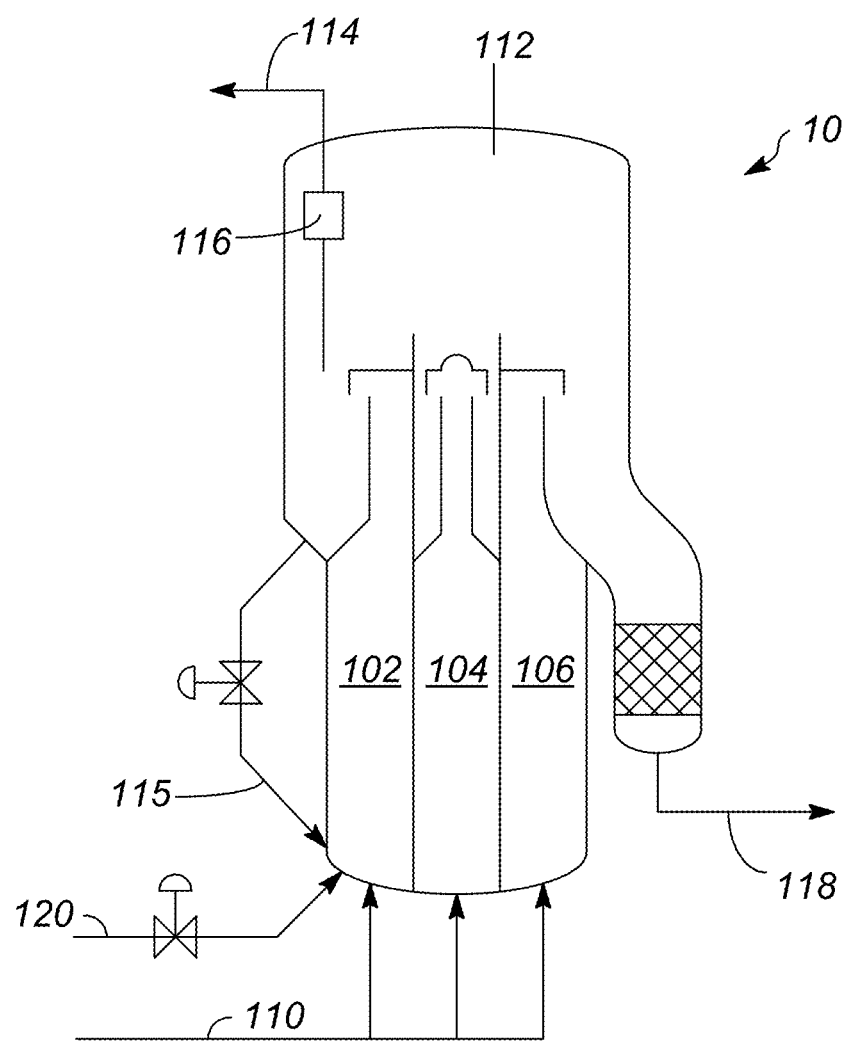
FIG. 2 is a schematic of a reactor having three reactor beds.

In one embodiment, the reactor comprises at least three reactor beds, as shown in FIG. 2. Fresh or regenerated catalyst is fed into the first reactor bed 102, and catalyst leaving the first reactor bed 102 flows to a second reactor bed 104. The catalyst leaving the second reactor bed 104 flows into the third reactor bed 106, with catalyst exiting the third reactor bed 106 being routed to a catalyst regeneration unit 20. A hydrocarbon feedstream 110 comprising paraffins is fed to each of the reactor beds 102, 104, 106 in parallel. In accord with reactor design, the reaction products from the reactor beds, 102, 104, and 106, separate from solid catalyst in a zone 112 above the beds. The reaction products exit the reactor through line 114. The reaction products are initially passed through a separator 116, such as a cyclone separator, to separate any catalyst fines generated in the reactor beds 102, 104, and 106. Spent catalyst or catalyst carried into the separation zone 112, is passed to the regeneration unit 20 through line 118.

The operation of the parallel reactor beds allows for a minimization of the hydrogen partial pressure in the reactor 10. The feedstream 110 is frequently premixed with a hydrogen stream, such that the feed to the reactors is a combined hydrocarbon-hydrogen feedstream to the reactor 10. However, with the present invention, the amount of hydrogen at the inlet to the reactor 10 can be reduced such that the hydrogen to hydrocarbon ratio is zero at the reactor inlet.

The design allows for a common separation system over all of the reactor beds, where catalyst fines and suspended catalyst are removed from the product stream before passing the product stream out of the reactor. The product stream can be used to preheat, or partially preheat, the hydrocarbon feedstream to the reactor 10.

In one embodiment, fresh or regeneration catalyst 120 enters the first reactor bed 102. A first feedstream flows through the first reactor bed, a stream comprising product and catalyst is carried out of the first reactor bed 102. The catalyst is separated from the product stream and at least partially directed to the second catalyst bed 104. A portion of the catalyst 115 can be recycled to the first reactor bed 102. A second feedstream flows through the second reactor bed 104, where a stream comprising product and catalyst is carried out of the second reactor bed 104. The catalyst from the second bed 104 is separated from the product stream and at least partially directed to the third catalyst bed 106. A third feedstream is fed to and flows through the third reactor bed 106. The catalyst is separated from the product stream and at least partially passed to the regeneration unit 20. The residence time of the hydrocarbons can be minimized while maintaining longer times for the catalyst in the reactors. In turn, the feedstreams can be split in different amounts to account for aging of the catalyst, and changing temperatures across the reactor system 10.

Figure 3:
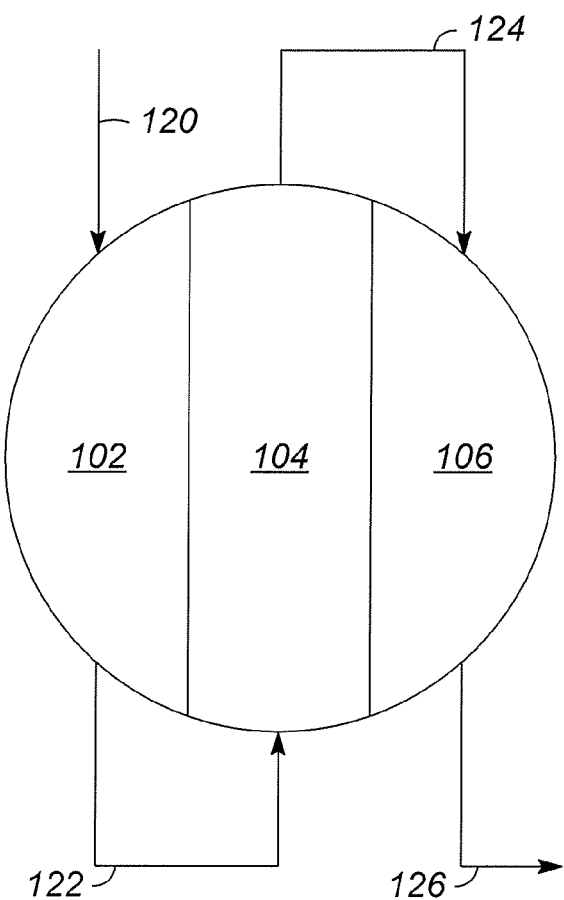
FIG. 3 is a schematic of the three reactor beds showing the flow of catalyst between the reactor beds.

In a specific embodiment, the catalyst flows do not need to be separated from the product stream. While it is mentioned that the catalyst flows do not need to be separated from the product stream, it is meant that there is a disengagement of the catalyst from the product stream before passing the catalyst between the reactor beds. It is not necessary to achieve the separation associated with passing the catalyst and product stream to a separation unit, such as including a cyclone, before passing the product stream out of the reactor. As shown in FIG. 3, the catalyst can move through the reactor beds 102, 104, 106 without having to be separated from the product stream. Fresh, or regenerated, catalyst is added to the first reactor bed 102 at the bottom of the reactor bed. The catalyst flows up through the reactor bed, and flows out the top of the reactor bed. The catalyst from the top of the first reactor bed 102 is directed to the bottom of the second reactor bed 104 through a channel 122 connecting the top of the first reactor bed 102 to the bottom of the second reactor bed 104. Catalyst flows up through the second reactor bed 104 and is collected from the top of the second reactor bed 104. The catalyst is passed by a channel 124 to the bottom of the third reactor bed 106. The catalyst then flows up through the third reactor bed 106, and is drawn off the top of the reactor bed. The catalyst drawn off the final reactor bed is then passed through a channel 126 to the regeneration unit 20. This provides a series flow of catalyst through the reactor beds. In each reactor bed, the hydrocarbon feedstream makes only one pass and is collected at the top of the reactor beds. While the drawings indicate three reactor beds, it is within the scope of this invention to have more than three reactor beds.

In addition, the system can include recycle channels to pass catalyst from the top of one reactor bed to the bottom of the same bed. This increases the average time the catalyst spends within one bed, provides density control and allows for additional heating of the catalyst during the passage through a recycle channel. Likewise, with the recycle channels, if the catalyst needs cooling, the catalyst temperature can be reduced before feeding the catalyst back into the reactor beds.

In another embodiment, each reactor bed can include a catalyst inlet for admitting regenerated catalyst. With this embodiment, the largest flow of regenerated catalyst is to the first reactor bed, with decreasing amounts of regenerated catalyst to each subsequent reactor bed. Using differential flow of regenerated catalyst to the reactor beds provides primarily for temperature control, but also provides for adjustment in catalytic activity.

One aspect of the present invention provides for a process for the dehydrogenation of hydrocarbons. The process comprises passing a hydrocarbon feedstream comprising paraffins in parallel to a plurality of fluidized reactor beds, where each reactor bed will generate a dehydrogenated product stream. Regenerated catalyst is passed to the first reactor bed of the plurality of reactor beds. As catalyst passes through the first fluidized reactor bed, partially spent catalyst exits the first reactor bed. The partially spent catalyst is then passed to a second reactor bed. The catalyst in the second reactor bed passes through the fluidized reactor bed, and is increasingly deactivated, thereby creating a further deactivated catalyst. This further deactivated catalyst is passed to a third reactor bed and flows through the fluidized reactor bed, thereby generating a spent catalyst stream. The spent catalyst is passed to a regeneration unit for regeneration of the catalyst. After regenerating the catalyst, the regenerated catalyst is passed to the first reactor bed.

The process of the present invention can be configured in numerous ways, but the preferred design utilized passing the catalyst into the reactor at the bottom of the reactor bed. The catalyst and hydrocarbon feedstream produces a fluidized bed that flow upward through the reactor bed. Catalyst is recovered at the top of the reactor bed from each reactor, and passed to the bottom of the reactor bed of a subsequent reactor bed.

For a dehydrogenation process, the reaction is endothermic, and additional heat is needed to maintain the reactor temperatures. The catalyst as it is drawn off can be passed through a heating unit, and catalyst can be recycled in one or more of the reactor beds, where catalyst is drawn off the top of a reactor bed and returned to the bottom of the same reactor bed. The amount of heating of catalyst and the average residence time of catalyst in an individual reactor bed can be controlled through this recycle, as well as the required catalyst circulation rate between the reactor and the regenerator.

The process can include passing lesser portions of regenerated catalyst to the second and/or third reactor beds. While the regenerated catalyst is generally passed to the first reactor bed, and the catalyst is allowed to cascade through the multiple reactor beds, a portion of the regenerated catalyst can be passed to subsequent reactor beds, i.e. the second and third reactor beds. The passing of lesser amounts of regenerated catalyst to the second and third reactor beds can provide control over the overall selectivity and conversion and operating temperature within a given reactor bed.

The operation of the dehydrogenation reaction includes operating the reactors at a pressure between 100 kPa and 500 kPa (14.5 psia to 72.5 psia), and preferably between 100 kPa and 300 kPa. The temperature of the reactors is operated in a range from 550° C. and 700° C. The reaction is operated under a hydrogen partial pressure, and the hydrogen to hydrocarbon mole feed ratio at the reactor inlets is less than 0.8. Since this new design provides for high selectivity and conversion while maintaining a low residence time for the catalyst, the process can be operated at hydrogen to hydrocarbon ratios near zero at the inlet. The level of hydrogen partial pressure depends on the type of catalyst used, and for many catalysts cannot be reduced to zero for optimum operation. The parallel nature of the beds with respect to the feedstream allows for hydrogen minimization at the inlet. The preferred usage is the production of propylene, and the preferred hydrocarbon feedstream is one which comprises propane. Another preferred hydrocarbon feedstream is butanes for the production of butylene.

The process, and design has been described with three reactor beds, but the process and design can be expanded to include more than three reactor beds, or can be for a two reactor bed system. The number of beds will be determined by the overall size of the dehydrogenation reactor system, the economics, and other variables normally encountered when designing a fluidized bed reactor system.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for dehydrogenation of hydrocarbons comprising:
    passing a hydrocarbon feedstream comprising paraffins to a plurality of reactor beds, wherein the hydrocarbon feedstream is passed in parallel to the reactor beds, thereby creating a dehydrogenated product stream, and wherein the reactor beds are fluidized reactor beds;
    passing a regenerated catalyst to the first reactor bed of the plurality of reactor beds;
    passing catalyst from the first reactor bed to a second reactor bed;
    passing catalyst from the second reactor bed to a third reactor bed;
    passing catalyst from the third reactor bed to a regeneration unit, thereby creating regenerated catalyst, wherein the catalyst has been passed through the reactor beds in series, wherein the temperature profile in the reactor beds is such that the temperature of the second bed is greater than the temperature of the first bed, and the temperature of the third bed is greater than the temperature of the second bed; and
    passing regenerated catalyst to the first reactor bed.

2. The process of claim 1 wherein there are three reactor beds, further comprising passing catalyst from the top of the first reactor bed to the bottom of the second reactor bed; and passing catalyst from the top of the second reactor bed to the bottom of the third reactor bed.

3. The process of claim 2 further comprising heating the catalyst passed from the top of each reactor bed to the bottom of the next reactor bed.

4. The process of claim 1 wherein the catalyst passed from the first reactor bed to the second reactor bed is passed from the top of the first reactor bed to the bottom of the second reactor bed.

5. The process of claim 1 wherein the catalyst passed from the second reactor bed to the third reactor bed is passed from the top of the second reactor bed to the bottom of the third reactor bed.

6. The process of claim 1 further comprising passing a portion of the regenerated catalyst to the second reactor bed, and passing a portion of the regenerated catalyst to the third reactor bed.

7. The process of claim 6 wherein the portions of regenerated catalyst passed to the second and third reactor beds are less than the regenerated catalyst passed to the first reactor bed.

8. The process of claim 1 further comprising a hydrogen to hydrocarbon mole feed ratio at the reactor inlets of less than 0.8.

9. The process of claim 1 further comprising a reactor pressure between 100 kPa and 300 kPa.

10. The process of claim 1 further comprising a reactor temperature between 550° C. and 700° C.

11. The process of claim 1 wherein the paraffins in the hydrocarbon feedstream comprise propane, butanes, or a mix of propane and butane.

12. The process of claim 1 further comprising the hydrocarbon feedstream at the reactor inlet having a hydrogen to hydrocarbon ratio of zero.

13. A process for dehydrogenation of hydrocarbons comprising:
    passing a hydrocarbon feedstream comprising paraffins to a plurality of reactor beds, wherein the hydrocarbon feedstream is divided into divided portions and the divided portions of the hydrocarbon feedstream are passed in a parallel manner to each of the reactor beds, and wherein the reactor beds are fluidized reactor beds;
    passing catalyst through each reactor bed in a series arrangement, wherein regenerated catalyst flows into a first reactor bed, and the catalyst in the first reactor bed flows into a subsequent reactor bed, and the catalyst continues to flow through the reactor beds until it leaves a last reactor bed, wherein the temperature of each subsequent reactor bed is greater than the temperature of the preceding reactor bed;
    passing the catalyst from the last reactor bed to a regeneration unit;
    regenerating the catalyst, thereby creating a regenerated catalyst stream; and
    passing the regenerated catalyst stream to the first reactor bed.

14. The process of claim 13 further comprising recycling catalyst from the top of each catalyst bed to the bottom of the same catalyst bed.

15. The process of claim 14 further comprising heating the recycled catalyst.

16. The process of claim 13 further comprising a hydrogen to hydrocarbon mole feed ratio at the reactor inlets of less than 0.8.

17. The process of claim 13 further comprising a reactor pressure between 100 kPa and 300 kPa.

18. The process of claim 13 further comprising a reactor temperature between 550° C. and 700° C.

19. The process of claim 13 further comprising the hydrocarbon feedstream at the reactor inlet having a hydrogen to hydrocarbon ratio of zero.

* * * * *